United States Patent
Candau

(10) Patent No.: US 9,308,155 B2
(45) Date of Patent: Apr. 12, 2016

(54) PHOTOPROTECTIVE COMPOSITION AND SCREENING AGENTS FOR SAID COMPOSITION

(75) Inventor: Didier Candau, Bievres (FR)

(73) Assignee: L'OREAL, Paris (FR)

( * ) Notice: Subject to any disclaimer, the term of this patent is extended or adjusted under 35 U.S.C. 154(b) by 1699 days.

(21) Appl. No.: 11/988,292

(22) PCT Filed: Jul. 12, 2006

(86) PCT No.: PCT/IB2006/052361
§ 371 (c)(1),
(2), (4) Date: Mar. 28, 2008

(87) PCT Pub. No.: WO2007/007283
PCT Pub. Date: Jan. 18, 2007

(65) Prior Publication Data
US 2009/0110650 A1    Apr. 30, 2009

Related U.S. Application Data

(60) Provisional application No. 60/708,761, filed on Aug. 17, 2005.

(30) Foreign Application Priority Data

Jul. 13, 2005   (FR) ........................... 05 52211

(51) Int. Cl.
*A61K 8/29*     (2006.01)
*A61Q 17/04*    (2006.01)
*A61K 8/25*     (2006.01)
*A61K 8/02*     (2006.01)

(52) U.S. Cl.
CPC ............. *A61K 8/25* (2013.01); *A61K 8/0241* (2013.01); *A61K 8/0258* (2013.01); *A61K 8/29* (2013.01); *A61Q 17/04* (2013.01); *A61K 2800/436* (2013.01); *A61K 2800/437* (2013.01)

(58) Field of Classification Search
CPC .................. A61K 2800/436; A61K 2800/437; A61K 8/0241; A61K 8/0258; A61K 8/25; A61K 8/29; A61Q 17/04
See application file for complete search history.

(56) References Cited

U.S. PATENT DOCUMENTS

| | | |
|---|---|---|
| 2,463,264 A | 3/1949 | Graenacher et al. |
| 4,077,441 A | 3/1978 | Rosen et al. |
| 4,434,010 A | 2/1984 | Ash |
| 4,850,517 A | 7/1989 | Ter Stege |

(Continued)

FOREIGN PATENT DOCUMENTS

| | | |
|---|---|---|
| DE | 19726 184 A1 | 12/1998 |
| DE | 197 46 654 A1 | 2/1999 |

(Continued)

OTHER PUBLICATIONS

Diffey et al., "A new substrate to measure sunscreen protection factors throughout the ultraviolet spectrum," *J. Soc. Cosmet. Chem.*, vol. 40, pp. 127-133, May/Jun. 1989.

(Continued)

*Primary Examiner* — Ernst V Arnold
(74) *Attorney, Agent, or Firm* — Oliff PLC

(57) ABSTRACT

The present invention concerns a photoprotective composition comprising at least one interferential screening agent screening UVA and/or UVB.

37 Claims, 1 Drawing Sheet

(56) References Cited

U.S. PATENT DOCUMENTS

| | | |
|---|---|---|
| 5,135,812 A | 8/1992 | Phillips et al. |
| 5,166,355 A | 11/1992 | Leistner et al. |
| 5,237,071 A | 8/1993 | Leistner et al. |
| 5,624,663 A | 4/1997 | Deflandre et al. |
| 5,902,569 A | 5/1999 | Oshima et al. |
| 6,187,298 B1 * | 2/2001 | Kurz et al. .................... 424/59 |
| 6,902,807 B1 * | 6/2005 | Argoitia et al. .............. 428/403 |
| 6,947,111 B2 * | 9/2005 | Li et al. ......................... 349/115 |
| 2003/0210373 A1 * | 11/2003 | Li et al. ......................... 349/138 |
| 2003/0224164 A1 * | 12/2003 | Argoitia et al. .............. 428/403 |
| 2004/0136931 A1 * | 7/2004 | Rozot ............................ 424/59 |
| 2004/0241189 A1 | 12/2004 | Ishii et al. |

FOREIGN PATENT DOCUMENTS

| | | |
|---|---|---|
| DE | 197 55 649 A1 | 6/1999 |
| DE | 198 55 649 A1 | 6/2000 |
| DE | 101 62 844 A1 | 7/2003 |
| EP | 0 133 981 A2 | 3/1985 |
| EP | 0 669 323 A1 | 8/1995 |
| EP | 0 832 642 A2 | 4/1998 |
| EP | 0 893 119 A1 | 1/1999 |
| EP | 0 967 200 A1 | 12/1999 |
| EP | 1 008 586 A1 | 6/2000 |
| EP | 1 027 883 A2 | 8/2000 |
| EP | 1 133 980 A2 | 9/2001 |
| EP | 1 300 137 A2 | 4/2003 |
| EP | 1477 154 A1 | 11/2004 |
| FR | 2 315 991 A1 | 1/1977 |
| FR | 2 416 008 A1 | 8/1979 |
| GB | 2 303 549 A | 2/1997 |
| WO | WO 92/06778 A1 | 4/1992 |
| WO | WO 93/04665 A1 | 3/1993 |

OTHER PUBLICATIONS

Prahl et al., "The Adding-Doubling Method," *Optical Thermal Response of Laser Irradiated Tissue*, Plenum Press, New York, pp. 101-129, 1995.

Prahl et al., "Photon Tissue Interaction," *Optical Society of America Annual Meeting*, p. 44, Nov. 4, 1991.

Prahl et al., "Determining the optical properties of turbid media by using the adding-doubling method," *Applied Optics*, vol. 32, No. 4, pp. 559-568, Feb. 1, 1993.

Deumie et al., "Overcoated microspheres for specific optical powders," *Applied Optics*, vol. 41, No. 16, pp. 3299-3305, Jun. 1, 2002.

Argoitia ct al., "Pigments Exhibiting Diffractive Effects," *Society of Vacuum Coaters—45th Annual Technical Conference Proceedings*, 505/856-7188, pp. 539-545, 2002.

Schlossman, "Treated Pigments: New Ways to Impart Color on the Skin," *Cosmetics & Toiletries*, vol. 105, pp. 53-64, Feb. 1990.

Bangham et al., "Diffusion of Univalent Ions across the Lamellae of Swollen Phospholipids," *J. Mol. Biol.*, vol. 13, pp. 238-252, 1965.

* cited by examiner

PHOTOPROTECTIVE COMPOSITION AND SCREENING AGENTS FOR SAID COMPOSITION

The present invention relates to photoprotective compositions, also sometimes termed sun screens, and to screening agents intended to absorb ultraviolet radiation in said compositions.

BACKGROUND

The quality of UVA (320-400 nm [nanometer]) and/or UVB (280-320 nm) screening is linked to the degree of absorption and to the screening bandwidth of the screening agents present in the composition.

Current photoprotective compositions use the following as screening agents:
soluble or insoluble organic screens; and/or
inorganic pigments.

As regards the first category, the absorption spectrum is rarely broad enough to cover the whole UV spectrum. Combinations are necessary.

As regards the second category, the screening effect is due to absorption, and also due to light diffusion phenomena. Thus, the spectrum is broader due to those phenomena.

While diffusion can broaden the screening spectrum, it reduces selectivity and the compositions may appear slightly colored, which is not desirable if the user wants to have a natural appearance.

U.S. Pat. No. 6,187,298 discloses pigments having an interferential multilayered structure intended to be incorporated into photoprotective compositions to screen infrared and visible radiation and produce a coppery color by interference.

A need exists to combine both screening with high spectral selectivity and also satisfactory transparency in the visible region.

The aim of the invention, inter alia, is to satisfy this requirement. The invention resides in the idea that certain interferential pigments may prove effective in achieving this objective, namely being sufficiently colorless and transparent in the visible region and relatively opaque in the UV region.

BRIEF DESCRIPTION OF THE DRAWINGS

Embodiments will be better understood from the detailed description given below and by reference to the attached drawings, in which.

DETAILED DESCRIPTION

Photoprotective Composition

Figure 1:
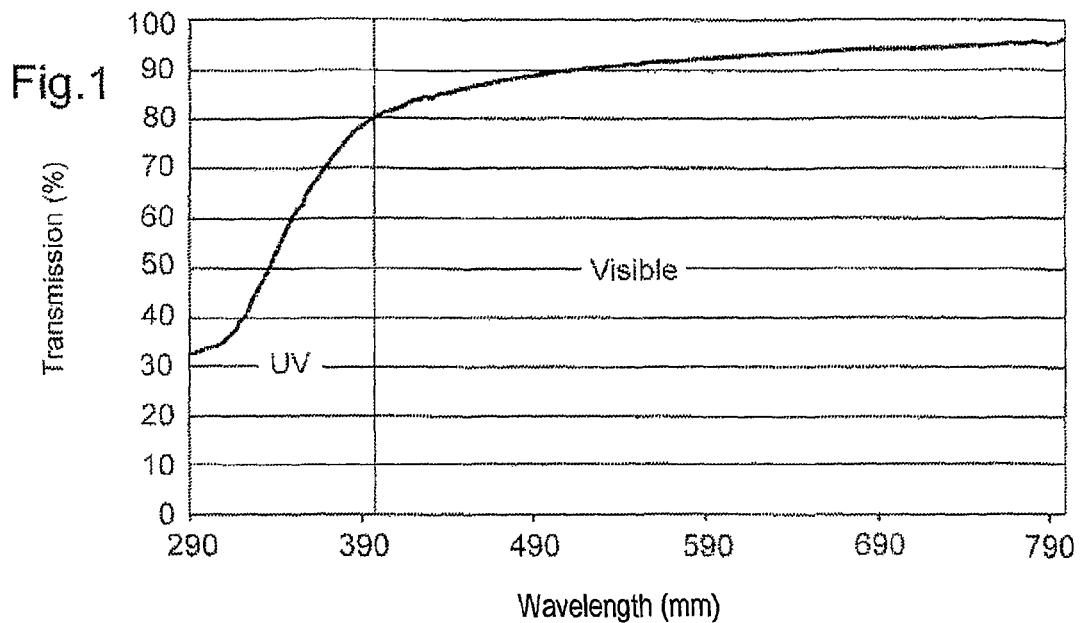
FIG. 1 is an illustration of an exemplary transmission spectra acquired from 290 nm to 800 nm using a UV-VIS spectrometer.

In an exemplary embodiment, the invention provides a photoprotective composition which comprises at least one interferential screening agent screening UVA and/or UVB.

The term "photoprotective composition" means a cosmetic composition in which the interferential screening agent actively participates in protection. A photoprotective composition has an SPF of at least 15, for example, and preferably at least 30, 45 or 60. The SPF (sunscreen protection factor) is defined in the article "A new substrate to measure sunscreen protection factors throughout the ultraviolet spectrum", J. Soc. Cosmet. Chem., 40, 127-133 (May/Jun. 1989) which is hereby incorporated by reference.

The interferential screening agent may be selected so that the composition has:
a transmission factor of 80% or more, preferably 85%, more preferably 90%, or even 95% over a band that is at least 200 nm wide, preferably at least 300 nm or even 400 nm wide in the 400-800 nm range; and
a transmission factor of 80% or less, preferably 70%, 60%, 50%, 40%, 30%, 20%, 10%, 5% or less, or more preferably 1% or less for at least one wavelength in the 290-400 nm range, or over the whole of said range.

A relatively high transmission factor in the 400 nm-800 nm range, for example over a wide range of incident angles, for example 0 to 80°, means that the natural appearance of the user is not unduly affected, while a low transmission factor in the 290-400 nm range ensures UV radiation screening.

In an exemplary embodiment, the invention may provide a photoprotective composition comprising an interferential UVA and/or UVB screening agent comprising at least one diffraction grating or an interferential multilayered structure.

The quantity of interferential screening agent may be adjusted as a function of the desired absorption in the UVA and/or UVB regions and the screening power of said agent.

Measurement of Transmission Factor of the Composition

The composition is deposited in a polished quartz cell with an optical path length of 10 μm [micrometers]. The transmission spectrum is acquired with a UV-VIS spectrometer in the 290 nm-800 nm range, the spectrometer being provided with an integration sphere.

Interferential Screening Agent

In an exemplary embodiment, the invention may provide an interferential UVA and/or UVB screening agent arranged to have the following, for example over a wide range of angles of incidence, for example 0 to 80°:
a transmission factor of 80% or less, for example 70%, 60%, 50%, 40%, 30%, 20%, 10%, 5% or less, or 1% or less for at least one wavelength in the 290-400 nm range, for example over the whole of the 290-400 nm range;
a transmission factor of 80% or more, for example 85%, more preferably 90%, or 95% over a band that is at least 200 nm wide, preferably at least 300 nm or even 400 nm wide in the 400-800 nm range.

The highest transmission factor in the 400-800 nm range may be higher than the lowest transmission factor in the 290-400 nm range by a factor of at least 10.

In an exemplary embodiment, the invention may provide an interferential UVA and/or UVB screening agent, for incorporation into a photoprotective composition, including at least one diffraction grating or an interferential multilayered structure.

Said screening agent may have transmission factors as defined above in the visible and UV regions.

The multilayered structure may be calculated so as to have, for example, a transmission spectrum with a steep edge at 400 nm for good UV rejection, and transmission of less than 10%, preferably less than 5%, or less than 1% in the UV region, for example in the range from 280 nm to 400 nm.

The spectrum has a slope of 1 or more optical density units per 10 nm at 400 nm, for example.

Transmission may be greater than 80%, more preferably greater than 85% or 90%, or even greater than 95% in a band that is at least 200 nm wide, or at least 300 nm wide in the 400 nm-800 nm range, for angles of incidence in the range 0° to 80°, the structure being for example produced so that it has low sensitivity to the angle of incidence.

The interferential screening agent may optionally be incorporated into a colored composition.

Measurement of Transmission Factor of Screening Agent

A concentrated dispersion is produced by adding 2% of a suitable dispersing agent such as the stearate of the 12-hydroxystearic acid oligomer sold by Avecia under the trade name Solsperse 21000 or oxyethylenated (20 OE) sorbitan mono-laurate sold by Uniqema under the trade name Tween 20.

The dispersing agent and solvent are weighed in a beaker. It is heated in its entirety to 60-65° C. in a water bath.

The interferential screening agent is added by sprinkling tiny amounts into the vortex created by stirring using a deflocculator.

If necessary, it is reheated to 60-65° C.

Next, the dispersion is rendered finer by homogenizing using shear agitation such as that produced using a device with the trade name Ultra-Turrax sold by Ika.

Next, the concentrated dispersion is diluted by weighing solvent into a beaker to produce a final dispersion of 2.5% by weight of interferential screening agent.

The whole batch is heated to 60-65° C. in a water bath.

The concentrated dispersion is added, with stirring using an Ultra-Turrax device, and homogenization is continued until a dispersion is obtained which is as finely divided as possible while avoiding overheating it too much.

The transmission spectra are acquired from 290 nm to 800 nm using a UV-VIS spectrometer provided with an integration sphere.

The base line correction is made with the solvent used to disperse the interferential screening agent.

Etched polished quartz cells with an optical path length of 10 μm are used.

The spectrum may, for example, have the shape shown in FIG. 1, although such a spectrum is not limiting.

In one implementation of the invention, the transmission factor for the interferential screening agent for at least one wavelength in the 290-400 nm range may be 80% or less, preferably 70% or less, more preferably 60%, 50%, 40%, 30%, 20%, 10%, 5% or less, or more preferably 1% or less.

In one implementation, the transmission factor may, for example be 10% or less, preferably 3% or less or 1% or less, over the whole of the 290-400 nm range.

The transmission factor for the screening agent may be 80% or more, 85% or more or 90% or more, preferably 95% or more, over at least one wavelength band in the 400 nm-800 nm range, for example over at least one interval which is 200 nm wide, preferably 300 nm wide in the 400 nm-800 nm range, or over the whole 400 nm-800 nm range.

The highest transmission factor in the 400 nm-800 nm range may be greater than the lowest transmission factor in the 290 nm-400 nm range by a factor of at least 10.

The interferential screening agent may be particulate in form.

The particles may have a flattened form; in this case, the mean dimension may not exceed 10 μm. The term "mean dimension" means the statistical granulometric dispersion at half the population, termed D50.

The particles may also optionally be spherical in form, with a diameter in the range 5 nm to 500 nm, in the range 10 nm to 250 nm, for example.

The interferential screening agent particles may optionally comprise an organic or inorganic substrate covered by an interferential or diffracting multilayered structure.

The substrate may, for example, have a refractive index of close to 1.5. As an example, it may be selected from metal oxides such as titanium dioxide, zinc oxide, zirconium oxide, boron nitride, silica, alumina, mica, zeolite, etc, or from organic compounds, polymers such as polymethyl methacrylate (PMMA), polyamides, in particular Nylon®, fluorinated polymers, in particular Tefon®, polyethylene teraphthalate (PET), etc.

Interferential Screening Agent with Multilayered Interferential Structure

The interferential screening agent may comprise a multilayered interferential structure.

The interferential structure may thus screen light by destructive interference between the light waves reflected by the various layers in the structure (for example by Fresnel type reflections).

In an embodiment, the multilayered structure may be selected to have a high transmission factor in the visible region, so that a marked color is not produced in the visible region and so that it has the desired transparency.

Said interferential multilayered structure may comprise alternating layers of low and high refractive indices. The difference in refractive index between the layers of low and high index may, for example, be 0.1 or more, preferably 0.15, or 0.6.

The number of the above-mentioned alternating layers may, for example, be at least 2, for example 4 or 6, or even at least 12, which makes it easier to produce a structure that has low sensitivity to the angle of incidence of the light and that has the required selectivity. The structure may optionally be symmetrical, and be capable of screening incident light regardless of the principal face allowing light into the structure, if appropriate.

The high refractive index material may be a mineral, for example titanium dioxide in the anatase or rutile form, an iron oxide, zirconium dioxide, zinc oxide, zinc sulfide, bismuth oxychloride, and mixtures thereof, or it may be organic, for example selected from: PEEK (polyether-ether-ketone), polyimide, PVN (poly(2-vinylnaphthalene)), PVK (poly(N-vinyl carbazole)), PF (phenol-formaldehyde resin), PSU (polysulfone resin), PaMes (poly(alpha-methylstyrene)), PVDC (poly(vinylidene chloride)), MeOS (poly(4-methoxy-styrene)), PS (polystyrene), BPA (bisphenol-A polycarbonate), PC (polycarbonate resin), PVB (Poly(vinyl benozoate)), PET (poly(ethylene terephthalate)), PDAP (poly(diallyl phthalate)), PPhMA (poly(phenyl methacrylate)), SAN (styrene/acrylonitrile copolymer), HDPE (high density polyethylene), PVC (polyvinyl chloride), NYLON®, POM (poly (oxymethylene) or polyformaldehyde), PMA (poly(methyl acrylate)), etc., and mixtures thereof.

The low refractive index material may be mineral, for example selected from silicon dioxide, magnesium fluoride, aluminum oxide, and mixtures thereof, or it may be organic, for example selected from polymers such as polymethylmethacrylate or polystyrene, polyurethane, and mixtures thereof.

To produce the interferential structure, the characteristics of the structure as a function of the layer thickness, their nature and their number may be simulated using suitable software.

The characteristics may, for example, be simulated using the method known as "adding-doubling" described in PRAHL, S.A. publications (1995), "*The Adding-Doubling Method*", in Optical Thermal Response of Laser Irradiated Tissue (Eds., Welch, A. J. and van Gemert, M. J. C.) Plenum Press, New York, pp. 101-129; S. A. Prahl and N. van Wieringen and M. J. C. van Gemert and A. J. Welch, "*Iterated* adding-doubling to determine optical properties", Optical Society of America, Nov. "1991"; S. A. Prahl and M. J. C. van Gemert and A. J. Welch, "*Determining the optical properties of turbid media by using the adding-doubling method*" Appl. Opt., 1993. 32. 559-568, which are hereby incorporated by reference. The starting point for that method is knowing the transmission and reflective properties of a thin layer of the medium under consideration. The layer must be sufficiently thin so that a photon traversing it will undergo a single absorption or diffusion.

Transmission and reflection of a layer twice as thick may be calculated by juxtaposing two identical layers, summing the contributions of each. This constitutes doubling. The properties of an arbitrary thickness of medium may be obtained by repeating the doubling until the desired thickness is reached.

Adding is based on the same principle, but instead of juxtaposing identical layers by doubling the thicknesses, adding adds two layers which may be of different natures, but with known properties. Adding allows internal reflections due to a discontinuity between different layers to be considered. The combination of adding and doubling allows the transmission and reflection of a stack of layers of different natures and any thickness to be calculated.

To produce interferential particles in a multilayered structure, the skilled person may refer to a number of publications which deal with thin layer deposition, for example "*Overcoated Microspheres for Specific Optical Powers*", in the review Applied Optics, Vol. 41, No 6 dated Jan. 6, 2002, hereby incorporated by reference, and patents from FLEX-PRODUCTS.

The various interfering layers of the multilayered structure may constitute the whole of the interferential screening agent, in the form of wafers or hollow spheres.

The various layers may also optionally be deposited on an organic or mineral substrate, as mentioned above, the multilayered structure then being used as is, or possibly undergoing a substrate dissolving treatment during manufacture.

Layers may be deposited on the substrate using known techniques such as vacuum deposition. After deposition, the substrate may be fragmented to produce particles, for example using ultrasound.

| Proposed Example (proportions by weight) | |
| --- | --- |
| PHASE A | |
| Polydimethylsiloxane | 0.5 |
| Preservatives | 1 |
| Stearic acid | 1.5 |
| Mixture of glyceryl mono-stearate/PEG stearate (100 OE) | 1 |
| Mixture of cetylstearyl glucoside and cetyl, stearyl alcohols | 2 |
| Cetyl alcohol | 0.5 |
| 4-tertiobutyl-4'-methoxy-dibenzoylmethane | 2 |
| bis {ethyl-hexyloxy-2-hydroxy-phenyl}-6-(methoxy-phenyl)-1,3,5-triazine | 3 |
| Interferential screening agent with interferential multilayered structure of invention | 10 |
| Benzoate of $C_{12}$-$C_{13}$ alcohols | 5 |
| Octocrylene | 10 |
| PHASE B | |
| Deionized water | Quantity sufficient for 100 |
| Complexing agent | 0.1 |
| Glycerol | 5 |
| Xanthan gum | 0.2 |
| Terephthalylidene dicamphor sulfonic acid | 1 |
| PHASE C | |
| Iso-hexadecane | 1 |
| Acrylic acid/stearyl methacrylate copolymer | 0.2 |
| Triethanolamine | Quantity sufficient for pH |

Operating Procedure:
 heat the aqueous phase (phase B) containing all of its ingredients to 80° C. in a water bath;
 heat the fatty phase (phase A) containing all of its ingredients to 80° C. in a water bath;
 emulsify A in B with rotor-stator type agitation (from Moritz);
 incorporate phase C and allow to cool to ambient temperature, with moderate stirring;
 introduce the triethanolamine to adjust the pH to the desired value at the end of manufacture.

Interferential Screening Agent with Diffracting Structure

The interferential screening agent may comprise a diffracting structure, for example at least one diffraction grating, which may be a grating comprising a surface relief (corrugation) which repeats noticeably in a manner that can diffract light.

The period of the grating and possibly the depth thereof determines, inter alia, the properties of diffraction of the grating.

The mark-space ratio of the diffraction grating may also be chosen to be unity.

The period of the diffraction grating, in at least one direction, may be small enough to reduce the risk of creating colored effects in the photoprotective composition. The period of the grating may thus be selected so that it does not diffract the light in the visible region, for example in the range 400 nm-780 nm.

The maximum period of the grating which can avoid having diffraction orders in the visible region may be determined in approximately by the relationship:

$$n_1 \sin\theta + \frac{m\lambda}{\Lambda} = n_2 \sin\Psi,$$

where $\theta$ is the angle of incidence measured with respect to the normal to the plane of the grating, $\Psi$ is the angle of transmission, $\Lambda$ is the period of the grating, m is the diffraction order, and $n_1$, and $n_2$ are the refractive indices of the incident medium and the transmission medium. $n_1$ and $n_2$ may be taken to be equal to 1.5 to a first approximation.

For $\theta=0°$, the maximum period $\Lambda$ is $\lambda/n_1=400/1.5 \simeq 267$ nm. With no limitation on the angle of incidence, the period is half that, i.e. $\Lambda \simeq 134$ nm.

Then, a period may be selected from the grating which is less than or equal to 270 nm, for example 140 nm or less.

The depth d of the grating and the period $\Lambda$ of the grating may be selected by successive trials to obtain a minimum transmission in the UVA region, for example.

The characteristics of the grating may be calculated by vectorial computation using GSOLVER software, for example, from GRATING SOLVER DEVELOPMENT COMPANY.

Figure 2:
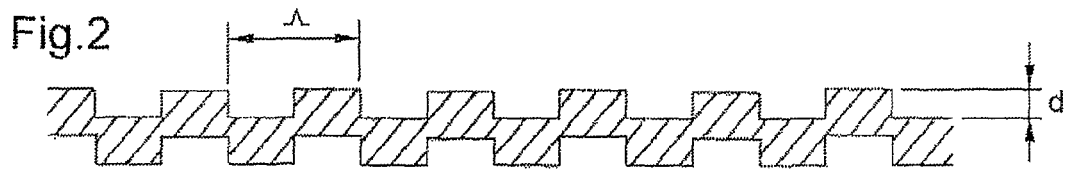
FIG. 2 is a diagrammatic representation of a diffracting structure.

FIG. 2 shows a diagrammatic representation of a diffracting structure which may exist on particles of an interferential screening agent produced in accordance with the invention.

The various layer(s) used to produce the diffracting structure may be mineral or organic and the particles of screening agent may optionally have a flat shape.

The various layer(s) used to produce the diffraction gratings may possibly be deposited on a substrate of an organic or mineral nature, which may be used as is or may subsequently undergo a dissolution treatment.

Hence, the structure of the grating or gratings may be etched either into the bulk of a material or after depositing a material on an organic or mineral substrate of spherical or lamellar form.

Etching may be carried out so that diffraction of the light in the visible region is a minimum, in order to minimize colored effects. The etching periodicity and its thickness determine the efficiency of the system in attenuating UV radiation.

The interferential screening agent may comprise two diffraction gratings which extend in non parallel directions, for example two substantially perpendicular directions, which can increase absorption in the UV of circularly polarized incident light and reduce the dependence of the screening performance on the angle of incidence.

The two diffraction gratings may have substantially equal periods $\Lambda_1$ and $\Lambda_2$, for example both 270 nm or less, for example 140 nm or less.

The two diffraction gratings may also have substantially equal depths, when they have a surface relief, and that relief can create a periodic variation in the index of the grating.

The period of the grating may be constant or varying and the depth may also be constant or varying.

The grating may extend in a rectilinear or curvilinear direction.

The diffraction grating may comprise a superimposition of layers having different refractive indices. The diffraction grating may be produced at least in part from a dielectric material.

The patterns of the grating or gratings may vary and, for example, have, in section, rectangular or triangular notches, sinusoidal undulations, or stepped notches.

The diffracting structure may be formed on at least a portion of the main face of the particle and for example on the two main faces of the particle. The diffracting structure may comprise a non-diffracting protective layer covering the gratings.

The composition may comprise a mixture of interferential UVA and/or UVB screening elements, for example particles having diffraction gratings having different periods and/or depths.

Figure 3:
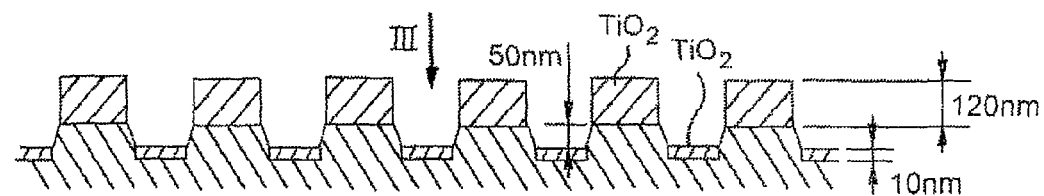
FIG. 3 is an exemplary illustration of a diffracting structure comprising two diffraction gratings.
Figure 4:
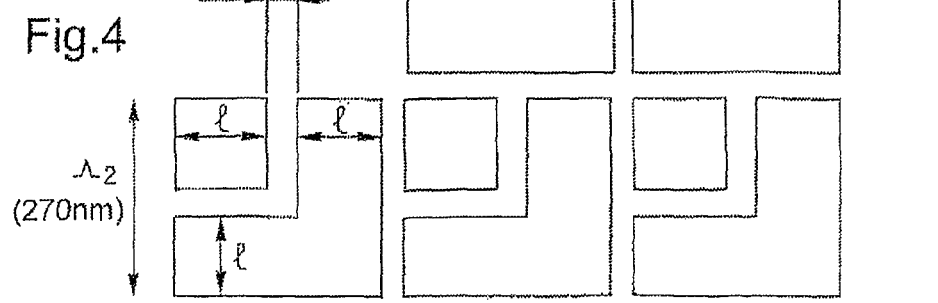
FIG. 4 is a cross-sectional illustration slowing a top view as seen looking along arrow IV of FIG. 3.

One example of a diffracting structure comprising two diffraction gratings is shown in section in FIG. 3, and FIG. 4 shows a top view as seen looking along arrow IV of FIG. 3. The dimensions given are purely by way of illustration. The gratings are, for example, formed by $TiO_2$ deposited on a silica substrate.

Manufacturing Process

An interferential diffracting structure may, for example, be manufactured by depositing a layer of a metal or a metal oxide, for example $TiO_2$, onto a substrate which is soluble in a solvent, in a vacuum chamber or by a sol-gel method.

The substrate may have portions in relief which can produce the relief of the grating. To produce said portions in relief it is possible, for example, to use a photolithographic etching technique, for example by holographic exposure(s) of a mask, followed by selective attack of the exposed and non exposed regions of the mask.

The diffracting structure on the particles may thus result from the formation on the mask of a repetitive pattern produced by interference, for example holographic exposure.

The publication *Pigments Exhibiting Diffractive Effects*, Alberto Argoitia and Matt Witzman, Flex Products Inc., Society of Vacuum Coaters 505/856-7188 45th Annual Technical Conference Proceedings (2002) ISSN 0737-5921, discloses an example of a process for manufacturing a colored diffractive pigment which may be useful in manufacturing an interferential screening agent of the invention.

After dissolving the substrate, the oxide layer may be fragmented into particles, for example by using ultrasound.

For large scale manufacture, equipment of the type employed for the manufacture of CHROMAFLAIR pigments from FLEX PRODUCTS may be used. Reference should be made to U.S. Pat. Nos. 5,135,812 and 4,434,010 the contents of which are herein incorporated by reference.

| Proposed Example (proportions by weight): | |
|---|---|
| COMPOSITION | |
| PHASE A | |
| Polydimethylsiloxane | 0.5 |
| Preservatives | 1 |
| Stearic acid | 1.5 |
| Mixture of glyceryl mono-stearate/PEG stearate (100 OE) | 1 |
| Mixture of cetylstearyl glucoside and cetyl, stearyl alcohol | 2 |
| Cetyl alcohol | 0.5 |
| 4-tertiobutyl-4'-methoxy-dibenzoylmethane | 2 |
| Bis {ethyl-hexyloxy-2-hydroxy-phenyl}-6-(methoxy-phenyl)-1,3,5-triazine | 1 |
| Interferential screening agent with diffracting structure* | 10 |
| Benzoate of $C_{12}$-$C_{13}$ alcohols | 5 |
| Octocrylene | 10 |
| PHASE B | |
| Deionized water | QSF 100 |
| Complexing agent | 0.1 |
| Glycerol | 5 |
| Xanthan gum | 0.2 |
| Terephthalylidene dicamphor sulfonic acid | 1 |
| PHASE C | |
| Iso-hexadecane | 1 |
| Acrylic acid/stearyl methacrylate copolymer | 0.2 |
| Triethanolamine | QSF pH |

*Particles with a diffracting structure comprising a grating with period $\Lambda$ = 140 nm and depth 25 nm, with a mark-space ratio of 1, a total thickness of 60 nm, produced from $TiO_2$.

Operating Procedure:
 heat the aqueous phase (phase B) containing all of its ingredients to 80° C. in a water bath;
 heat the fatty phase (phase A) containing all of its ingredients to 80° C. in a water bath;
 emulsify A in B with rotor-stator type agitation (from Moritz);
 incorporate phase C and allow to cool to ambient temperature, with moderate stirring;
 introduce the triethanolamine to adjust the pH to the desired value at the end of manufacture.

Complementary Screens

The composition of the invention may also comprise one or more complementary screening agents screening UV radiation, selected from organic and/or mineral screens which are active in the UVA and/or UVB region which are hydrophilic and/or lipophilic and/or practically insoluble in routinely used cosmetic solvents.

The hydrophilic, lipophilic, or insoluble UV screens are selected from the following: anthranilates; dibenzoylmethane derivatives; cinnamic derivatives; salicylic derivatives, camphor derivatives; benzophenone derivatives; β,β-diphenylacrylate derivatives; triazine derivatives; benzotriazole derivatives; benzalmalonate derivatives, in particular those described in U.S. Pat. No. 5,624,663; benzimidazole derivatives; imidazolines; bis-benzoazolyl derivatives, such as those described in European patent EP-A-0 669 323 and U.S. Pat. No. 2,463,264; p-aminobenzoic acid derivatives (PABA); methylene bis-(hydroxyphenyl benzotriazole) derivatives, such as those described in patent applications U.S. Pat. Nos. 5,237,071, 5,166,355, GB-A-2 303 549, DE-A-197 26 184 and EP-A-0 893 119; benzoxazole derivatives, such as those described in EP-A-0 832 642, EP-A-1 027 883, EP-A-1 300 137 and DE-A-10162844; polymeric and silicone screens, such as those described in International application WO-A-93/04665; dimers derived from α-alkylstyrene, such as those described in German patent application DE-A-19855649; 4,4-diarylbutadienes, such as those described in applications EP-A-0 967 200, DE-A-19746654, DE-A-19755649, EP-A-1 008 586, EP-A-1 133 980 and EP-A-0 133 981, and mixtures thereof.

Examples of organic UV screens that may be mentioned are those listed below using their INCI names:

Para-Aminobenzoic Acid Derivatives:
PABA,
Ethyl PABA,
Ethyl dihydroxypropyl PABA,
Ethylhexyl dimethyl PABA, sold under the trade name "ESCALOL 507" by ISP,
Glyceryl PABA,
PEG-25 PABA, sold under the trade name "UVINUL P25" by BASF.

Dibenzoylmethane Derivatives:
Butyl methoxydibenzoylmethane, sold under the trade name "PARSOL 1789" by HOFFMANN LAROCHE,
Isopropyl dibenzoylmethane.

Salicylic Derivatives:
Homosalate, sold under the trade name "Eusolex HMS" by Rona/EM Industries,
Ethylhexyl salicylate, sold under the trade name "NEO HELIOPAN OS" by Haarmann and REIMER,
Dipropyleneglycol salicylate sold under the trade name "DIPSAL" by SCHER,
TEA salicylate, sold under the trade name "NEO HELIOPAN TS" by Haarmann and REIMER.

Cinnamic Derivatives:
Ethylhexyl methoxycinnamate, sold under the trade name "PARSOL MCX" by HOFFMANN LA ROCHE,
Isopropyl methoxy cinnamate,
Isoamyl methoxy cinnamate, sold under the trade name "NEO HELIOPAN E 1000" by HAARMANN and REIMER,
Cinoxate,
DEA methoxycinnamate,
Diisopropyl methylcinnamate,
Glyceryl ethylhexanoate dimethoxycinnamate.

β,β-Diphenylacrylate Derivatives:
Octocrylene, sold under the trade name "UVINUL N539" by BASF,
Etocrylene, sold under the trade name "UVINUL N35" by BASF.

Benzophenone Derivatives:
Benzophenone-1, sold under the trade name "UVINUL 400" by BASF,
Benzophenone-2, sold under the trade name "UVINUL D50" by BASF, Benzophenone-3 or Oxybenzone, sold under the trade name "UVINUL M40" by BASF,
Benzophenone-4, sold under the trade name "UVINUL MS40" by BASF,
Benzophenone-5,
Benzophenone-6, sold under the trade name "Helisorb 11" by Norquay
Benzophenone-8, sold under the trade name "Spectra-Sorb UV-24" by American Cyanamid,
Benzophenone-9, sold under the trade name "UVINUL DS-49" by BASF,
Benzophenone-12,
n-hexyl 2-(4-diethylamino-2-hydroxybenzoyl)-benzoate.

Benzylidene Camphor Derivatives:
3-Benzylidene camphor, manufactured under the trade name "MEXORYL SD" by CHIMEX,
4-Methylbenzylidene camphor, sold under the trade name "EUSOLEX 6300" by MERCK,
Benzylidene camphor sulfonic acid, manufactured under the trade name "MEXORYL SL" by CHIMEX,
Camphor benzalkonium methosulfate made under the trade name "MEXORYL SO" by CHIMEX,
Terephthalylidene dicamphor sulfonic acid, sold under the trade name "MEXORYL SX" by CHIMEX,
Polyacrylamidomethyl benzylidene camphor, manufactured under the trade name "MEXORYL SW" by CHIMEX.

Phenyl Benzimidazole Derivatives:
Phenylbenzimidazole sulfonic acid, sold under the trade name "EUSOLEX 232" by MERCK,
Disodium phenyl dibenzimidazole tetra-sulfonate, sold under the trade name "NEO HELIOPAN AP" by Haarmann and REIMER.

Phenyl Benzotriazole Derivatives:
Drometrizole trisiloxane, sold under the trade name "Silatrizole" by RHODIA CHIMIE,
Methylene bis-benzotriazolyl tetramethylbutylphenol, sold in the solid form under the trade name "MIXXIM BB/100" by FAIRMOUNT CHEMICAL or in the micronized form in aqueous dispersion under the trade name "TINOSORB M" by CIBA SPECIALTY CHEMICALS.

Triazine Derivatives:
Bis-ethylhexyloxyphenol methoxyphenyl triazine sold under the trade name <<TINOSORB S" by CIBA GEIGY,
Ethylhexyl triazone, sold under the trade name <<UVINUL T150" by BASF,
Diethylhexyl butamido triazone, sold under the trade name "UVASORB HEB" by SIGMA 3V,
2,4,6-tris-(diisobutyl 4'-amino benzalmalonate)-s-triazine,
2,4,6-tris(dineopentyl 4'-amino benzalmalonate)-s-triazine.

Anthranilic Derivatives:
Menthyl anthranilate, sold under the trade name "NEO HELIOPAN MA" by Haarmann and REIMER.

Imidazoline Derivatives:
Ethylhexyl dimethoxybenzylidene dioxoimidazoline propionate.

Benzalmalonate Derivatives:
Di-neopentyl 4'-methoxybenzalmalonate,
Polyorganosiloxane with benzalmalonate functions, such as Polysilicone-15 sold under the trade name "PARSOL SLX" by HOFFMANN LA ROCHE.

4,4-Diarylbutadiene Derivatives:
1,1-dicarboxy(2,2'-dimethyl-propyl)-4,4-diphenylbutadiene.

Benzoxazole Derivatives:
2,4-bis-[5-1(dimethylpropyl)benzoxazol-2-yl-(4-phenyl)-imino]-6-(2-ethylhexyl)-imino-1,3,5-triazine, sold under the trade name "Uvasorb K2A" by Sigma 3V
and mixtures thereof.

Preferred organic UV radiation screening agents are selected from:
Ethylhexyl methoxycinnamate,
Homosalate,
Ethylhexyl salicylate,
Butyl methoxydibenzoylmethane,
Octocrylene,
Phenylbenzimidazole sulfonic acid,
Benzophenone-3,
Benzophenone-4,
Benzophenone-5,
n-hexyl 2-(4-diethylamino-2-hydroxybenzoyl)-benzoate,
4-Methylbenzylidene camphor,
Terephthalylidene dicamphor sulfonic acid,
Disodium phenyl dibenzimidazole tetra-sulfonate,
Ethylhexyl triazone,
Bis-ethylhexyloxyphenol methoxyphenyl triazine,
Diethylhexyl butamido triazone,
2,4,6-tris(dineopentyl 4'-amino benzalmalonate)-s-triazine,
2,4,6-tris-(diisobutyl 4'-amino benzalmalonate)-s-triazine,
Methylene bis-benzotriazolyl tetramethylbutylphenol,
Drometrizole trisiloxane,
Polysilicone-15,
Di-neopentyl 4'-methoxybenzalmalonate,
1,1-dicarboxy(2,2'-dimethyl-propyl)-4,4-diphenylbutadiene,
2,4-bis-[5-1(dimethylpropyl)benzoxazol-2-yl-(4-phenyl)-imino]-6-(2-ethylhexyl)-imino-1,3,5-triazine,
and mixtures thereof.

Inorganic screens may be selected from pigments or from nanopigments (mean particle size of primary particles: generally in the range 5 nm to 100 nm, for example in the range 10 nm to 50 nm) of coated or non-coated metal oxides such as nanopigments of titanium oxide (amorphous or crystalline in the form of rutile and/or anatase), iron, zinc, zirconium, or cerium which are all UV photoprotective agents which are well known per se.

The pigments may be coated or non-coated.

Coated pigments are pigments which have undergone one or more separate treatments of a chemical, electronic, mechanico-chemical and/or mechanical nature with compounds such as those described, for example, in Cosmetics & Toiletries, Feb. 1990, Vol. 105, p. 53-64, such as amino acids, beeswax, fatty acids, fatty alcohols, anionic surfactants, lecithins, sodium, potassium, zinc, iron or aluminum salts of fatty acids, metal alkoxides (titanium or aluminum), polyethylene, silicones, proteins (collagen, elastin), alkanolamines, silicon oxides, metal oxides, or sodium hexametaphosphate.

Silicones, of course, are organo-silicone polymers or oligomers with a linear or cyclic structure, branched or cross-linked, with various molecular weights obtained by polymerization and/or polycondensation of suitably functionalized silanes, and essentially constituted by a repeated series of principal patterns in which the silicon atoms are bonded together by oxygen atoms (siloxane linkage), optionally substituted hydrocarbon radicals being directly linked via a carbon atom to said silicon atoms.

The term "silicones" also encompasses the silanes necessary for their preparation, in particular alkylsilanes.

The silicones used to coat nanopigments suitable for the present invention may be selected from the group containing alkylsilanes, polydialkylsiloxanes, and polyalkyl hydrogen siloxanes. The silicones may be selected from the group containing octyl trimethylsilane, polydimethylsiloxanes, and polymethylhydrogen siloxanes.

Clearly, prior to their treatment with silicones, the metal oxide pigments may have been treated with other surface agents, for example with cerium oxide, alumina, silica, aluminum compounds, silicon compounds, or mixtures thereof.

Coated pigments may be titanium oxides coated with:
silica, such as "SUNVEIL" from IKEDA,
silica and iron oxide, such as "SUNVEIL F" from IKEDA,
silica and alumina, such as "MICROTITANIUM DIOXIDE MT 500 SA"; and "MICROTITANIUM DIOXIDE MT 100 SA" from TAYCA, "TIOVEIL" from TIOXIDE, and "Mirasun TiW 60" from Rhodia,
alumina, such as "TIPAQUE TTO-55 (B)" and "TIPAQUE TTO-55 (A)" from ISHIHARA, and "UVT 14/4" from KEMIRA;
alumina and aluminum stearate, such as "MICROTITANIUM DIOXIDE MT 100 T, MT 100 TX, MT 100 Z, MT-01 from TAYCA, "Solaveil CT-10 W" and "Solaveil CT 100" from UNIQEMA and "Eusolex T-AVO" from MERCK,
silica, alumina and alginic acid, such as "MT-100 AQ" from TAYCA,
alumina and aluminum laurate, such as "MICROTITANIUM DIOXIDE MT 100 S" from TAYCA,
iron oxide and iron stearate, such as "MICROTITANIUM DIOXIDE MT 100 F" from TAYCA,
zinc oxide and zinc stearate, such "BR351" from TAYCA,
silica and alumina treated with a silicone, such as "MICROTITANIUM DIOXIDE MT 600 SAS", "MICROTITANIUM DIOXIDE MT 500 SAS" or "MICROTITANIUM DIOXIDE MT 100 SAS" from TAYCA,
silica, alumina, aluminum stearate treated with a silicone, such as "STT-30-DS" from TITAN KOGYO,
silica treated with a silicone, such as "UV-TITAN X 195" from KEMIRA;
alumina treated with a silicone, such as "TIPAQUE TTO-55 (S)" from ISHIHARA or "UV TITAN M 262" from KEMIRA,
triethanolamine, such as "STT-65-S" from TITAN KOGYO,
stearic acid, such as "TIPAQUE TTO-55 (C)" from ISHIHARA,
sodium hexametaphosphate, such as "MICROTITANIUM DIOXIDE MT 150 W" from TAYCA.

Other titanium oxide pigments treated with a silicone may be $TiO_2$ treated with octyl trimethylsilane with a mean elementary particle size in the range 25 nm to 40 nm, such as that sold under the trade name "T 805" by DEGUSSA SILICES, $TiO_2$ treated with a polydimethylsiloxane with a mean elementary particle size of 21 nm, such as that sold under the trade name "70250 Cardre UF TiO2SI3" by CARDRE, anatase/rutile $TiO_2$ treated with a polydimethyl hydrogen siloxane with a mean elementary particle size of 25 nm, such as that sold under the trade name "MICRO TITANIUM DIOXYDE USP GRADE HYDROPHOBIC" by COLOR TECHNIQUES.

The non-coated titanium oxide pigments may, for example, be sold by TAYCA under the trade names "MICROTITANIUM DIOXIDE MT 500 B" or "MICROTITTANIUM DIOXIDE MT600 B", by DEGUSSA under the trade name "P 25", by WACKHER under the trade name "Oxyde de titane transparent PW", by MIYOSHI KASEI under the trade name "UFTR", by TOMEN under the trade name "ITS" and by TIOXIDE under the trade name "TIOVEIL AQ".

Examples of non-coated zinc oxide pigments are:
those sold under the trade name "Z-cote" by Sunsmart,
those sold under the trade name "Nanox" by Elementis,
those sold under the trade name "Nanogard WCD 2025" by Nanophase Technologies.

Examples of coated zinc oxide pigments are:
those sold under the trade name "Oxide zinc CS-5" by Toshibi (ZnO coated with polymethyl hydrogen siloxane),
those sold under the trade name "Nanogard Zinc Oxide FN" by Nanophase Technologies (in 40% dispersion in Finsolv TN, benzoate of $C_{12}$-$C_{15}$ alcohols),
those sold by "DAITOPERSION Zn-30" and "DAITOPERSION Zn-50" by Daito (dispersions in cyclopolymethylsiloxane/oxyethylenated polydimethylsiloxane, containing 30% or 50% of zinc nano-oxides coated with silica and polymethyl hydrogen siloxane),
those sold under the trade name "NFD Ultrafine ZnO" by Daikin (ZnO coated with perfluoroalkyl phosphate and copolymer based on perfluoroalkylethyl in dispersion in cyclopentasiloxane),
those sold under the trade name "SPD-Z1" by Shin-Etsu (ZnO coated with silicone grafted acrylic polymer dispersed in cyclodimethylsiloxane),
those sold under the trade name "Escalol Z100" by ISP (ZnO-treated alumina dispersed in ethylhexyl methoxycinnamate/PVP-hexadecene/methicone copolymer),
those sold under the trade name "Fuji ZnO-SMS-10" by Fuji Pigment (ZnO-coated silica and polymethylsilsesquioxane),
those sold under the trade name "Nanox Gel TN" by Elementis (55% dispersed ZnO in benzoate of $C_{12}$-$C_{15}$ alcohols with hydroxystearic acid polycondensate).

Non-coated cerium oxide pigments are, for example, sold under the trade name "COLLOIDAL CERIUM OXIDE" by RHONE POULENC.

Non-coated iron oxide nanopigments are, for example, sold by ARNAUD under the trade names "NANOGARD WCD 2002 (FE 45B)", "NANOGARD IRON FE 45 BL AQ", "NANOGARD FE 45R AQ, "NANOGARD WCD 2006 (FE 45R)", or by MITSUBISHI under the trade name "TY-220".

Coated iron oxide nanopigments are, for example, sold by ARNAUD under the trade names "NANOGARD WCD 2008 (FE 45B FN)", "NANOGARD WCD 2009 (FE 45B 556)", "NANOGARD FE 45 BL 345", "NANOGARD FE 45 BL", or by BASF under the trade name "OXYDE DE FER TRANSPARENT".

It is also possible to cite mixtures of metal oxides, for example titanium dioxide and cerium dioxide, including the equimass mixture of titanium dioxide and cerium dioxide coated with silica sold by IKEDA under the trade name "SUNVEIL A", as well as a mixture of titanium dioxide and zinc dioxide coated with alumina, silica and silicone, such as the product "M 261" sold by KEMIRA or coated with alumina, silica and glycerin, such as the product "M 211" sold by KEMIRA.

The UV screening agents including the interferential screening agents may be present in the compositions of the invention in proportions of 0.01% to 20% by weight with respect to the total composition weight, for example 0.1% to 10% by weight with respect to the total composition weight.

Other Compounds

The compositions of the invention may also contain artificial skin bronzing and/or tanning agents (self tanning agents), or dihydroxyacetone (DHA). They may be present in quantities of 0.1% to 10% by weight with respect to the total composition weight.

The aqueous compositions of the present invention may also comprise conventional cosmetic adjuvants, for example those selected from fats, organic solvents, ionic or non-ionic hydrophilic or lipophilic thickening agents, softeners, moisturizers, opacifying agents, stabilizing agents, emollients, silicones, anti-foaming agents, fragrances, preservatives, anionic, cationic, non-ionic, zwitterionic or amphoteric surfactants, active ingredients, fillers, polymers, propellants, alkalinizing or acidifying agents, or any other ingredient in routine use in the cosmetic, and/or dermatological field.

Fats may be constituted by an oil or a wax other than apolar waxes as defined above, or mixtures thereof. The term "oil" means a compound which is liquid at ambient temperature. The term "wax" means a compound which is solid or substantially solid at ambient temperature, with a melting point which is generally over 35° C.

Oils which may be cited are mineral oils (paraffin); vegetable oils (sweet almond oil, macadamia nut oil, blackcurrant seed oil, jojoba oil); synthetic oils such as perhydrosqualene, alcohols, fatty amides (such as isopropyl lauroyl sarcosinate sold under the trade name "Eldew SL-205" by Ajinomoto), fatty acids or esters (such as benzoate of $C_{12}$-$C_{15}$ alcohols sold under the trade name "Finsolv TN" or "Witconol TN" by WITCO, octyl palmitate, isopropyl lanolate, triglycerides including those of capric/caprylic acid, dicaprylyl carbonate sold under the trade name "Cetiol CC" by Cognis), oxyethylenated or oxypropylenated fatty esters or ethers, silicone oils (cyclomethicone, polydimethysiloxanes or PDMS), or fluorinated oils, and polyalkylenes.

Waxy compounds which may be cited are carnauba wax, beeswax and hydrogenated castor oil.

Organic solvents which may be cited are lower alcohols and polyols. These later may be selected from glycols and glycol ethers such as ethylene glycol, propylene glycol, butylene glycol, dipropylene glycol, or diethylene glycol.

Hydrophilic thickening agents which may be cited are carboxyvinyl polymers such as Carbopols (Carbomers) and Pemulens (acrylate/$C_{10}$-$C_{30}$ alkylacrylate copolymer); polyacrylamides such as cross-linked copolymers sold under the trade names Sepigel 305 (CTFA name: polyacrylamide/C13-14 isoparaffin/laureth 7) or Simulgel 600 (CTFA name: acrylamide/sodium acryloyldimethyltaurate copolymer/isohexadecane/polysorbate 80) by Seppic; polymers and copolymers of 2-acrylamido 2-methylpropane sulfonic acid, optionally cross-linked and/or neutralized, such as poly(2-acrylamido 2-methylpropane sulfonic acid) sold by Hoechst under the trade name "Hostacerin AMPS" (CTFA name: ammonium polyacryldimethyltauramide); cellulose derivatives such as hydroxyethylcellulose; polysaccharides and especially gums such as xanthan gum; and mixtures thereof.

Lipophilic thickening agents which may be cited are synthetic polymers such as poly C10-C30 alkyl acrylate sold under the trade name "Doresco IPA 13-1" by Landec or modified clays such as hectorite and its derivatives, such as the products sold under the trade name Bentone.

Active ingredients which may be cited include:
vitamins (A, C, E, K, PP, etc) and their derivatives or precursors, used alone or as a mixture;
antipollution agents and/or free radical scavengers;
de-pigmentation agents and/or pro-pigmentation agents;
anti-glycation agents;
soothing agents;
NO-synthase inhibitors;

agents stimulating the synthesis of dermal or epidermal macromolecules and/or preventing their degradation;
agents stimulating fibroblast proliferation;
agents stimulating keratinocyte proliferation;
myorelaxing agents;
tightening agents;
mattifying agents;
keratolytic agents;
desquamating agents;
moisturizing agents;
anti-inflammatory agents;
agents acting on cell metabolism;
insect repellents;
antagonists for P or CRGP substances;
hair loss prevention and/or hair regrowth agents;
anti-wrinkle agents.

Clearly, the skilled person may carefully select any of the complementary compounds cited above and/or their quantities so that the advantageous intrinsic properties of the compositions of the invention are not, or are not substantially, altered by the envisaged adjuvants.

Galenical Forms

The compositions of the invention may be prepared using techniques which are well known to the skilled person. They may in particular be in the form of an emulsion, simple or complex (O/W, W/O, O/W/O or W/O/W) such as a cream, milk or cream gel; in the form of an aqueous gel; or in the form of a lotion. They may optionally be packaged in aerosol form and be in the form of a foam or spray.

The compositions of the invention may be in the form of an oil-in-water or water-in-oil emulsion.

The emulsions may generally contain at least one emulsifying agent selected from amphoteric, anionic, cationic or non-ionic emulsifying agents, used alone or as a mixture.

The emulsifying agents may be selected in a suitable manner depending on the emulsion to be produced (W/O or O/W).

Examples of emulsifying surfactants which may be used to prepare W/O emulsions which may be cited include sorbitan, glycerol or sugar alkyl esters or ethers, silicone surfactants such as dimethicone copolyols such as the mixture of cyclomethicone and dimethicone copolyol sold under the trade name "DC 5225 C" by Dow Corning, and alkyl-dimethicone copolyols such as laurylmethicone copolyol sold under the trade name "Dow Corning 5200 Formulation Aid" by Dow Corning; cetyl dimethicone copolyol, such as the product sold under the trade name "Abil EM 90R" by Goldschmidt and the mixture of cetyl dimethicone copolyol, polyglycerol isostearate (4 moles) and hexyl laurate sold under the trade name "ABIL WE O9" by Goldschmidt. One or more co-emulsifying agents may be added thereto which may be selected from the group including polyol alkylated esters.

Examples of polyol alkylated esters which may be cited are polyethylene glycol esters such as PEG-30 dipolyhydroxystearate such as the product sold under the trade name "Arlacel P135" by ICI.

Examples of glycerol and/or sorbitan esters which may be cited include polyglycerol isostearate, such as the product sold under the trade name "Isolan GI34" by Goldschmidt; sorbitan isostearate such as the product sold under the trade name "Arlacel 987" by ICI; sorbitan isostearate and glycerol, such as the product sold under the trade name "Arlacel 986" by ICI, and mixtures thereof.

For O/W emulsions, examples which can be cited as emulsifying agents are non-ionic emulsifying agents such as oxyalkylenated (more particularly polyoxyethylenated) esters of fatty acids and glycerol; oxyalkylenated esters of fatty acids and sorbitan; oxyalkylenated (oxyethylenated and/or oxypropylenated) esters of fatty acids such as the PEG-100 stearate/glyceryl stearate mixture sold, for example, by ICI under the trade name "Arlacel 165"; oxyalkylenated (oxyethylenated and/or oxypropylenated) ethers of fatty alcohols; esters of sugars such as sucrose stearate; ethers of fatty alcohol and sugar, for example alkylpolyglucosides (APG) such as decylglucoside and laurylglucoside sold, for example, by Henkel under the trade name "Plantaren 2000" and "Plantaren 1200" respectively, cetostearylglucoside, optionally mixed with cetostearyl alcohol sold, for example, under the trade name "Montanov 68" by Seppic, under the trade name "Tegocare CG90" by Goldschmidt and under the trade name "Emulgade KE3302" by Henkel, as well as arachidyl glucoside, for example in the form of a mixture of arachidic alcohol and behenic alcohol and arachidylglucoside sold under the trade name "Montanoc 202" by Seppic. In an implementation of the alkylpolyglucoside mixture defined above with the corresponding fatty alcohol may be in the form of a self-emulsifying composition as described, for example, in WO-A-92/06778.

As regards an emulsion, the aqueous phase may comprise a non-ionic vesicular dispersion prepared using known processes (Bangham, Standish and Watkins. J. Mol. Biol. 13, 238 (1965), FR-A-2 315 991 and FR-A-2 416 008).

The compositions of the invention may be of application in a large number of treatments, for example cosmetic, for the skin, lips, and hair, including the scalp, to protect and/or care for the skin, lips, and/or hair, and/or to make up the skin, and/or lips.

In an embodiment, the invention may concern the use of compositions of the invention as defined above for the manufacture of cosmetics for treating the skin, lips, nails, hair, eyebrows, eyelashes, and/or scalp, for example care products, sun screens, and makeup.

The cosmetic compositions of the invention may, for example, be used as a care product and/or sunscreen for the face and/or the body, with a liquid to semi-liquid consistency, such as lotions, milks, creams which are oily to a greater or lesser extent, gels, or gel-creams. They may also be packaged in aerosol form and be in the form of a foam or spray.

Compositions of the invention in the form of vaporizable fluid lotions of the invention may be applied to the skin or hair in the form of fine particles using pressurized derivatives. Devices for use with the invention are known in the art and include non aerosol pumps or atomizers, aerosol receptacles comprising a propellant and aerosol pumps using compressed air as the propellant. These latter have been described in U.S. Pat. Nos. 4,077,441 and 4,850,517 (forming an integral part of the contents of the description).

Compositions packaged in aerosol form for use with the invention may generally contain conventional propellants such as hydrofluorinated compounds, for example dichlorodifluoromethane, difluoroethane, dimethylether, isobutane, n-butane, propane, or trichlorofluoromethane. They may for example be present in quantities of 15% to 50% by weight with respect to the total composition weight.

The invention claimed is:

1. A photoprotective composition comprising at least one interferential screening agent screening UVA and/or UVB, said screening agent comprising a diffracting structure comprising at least one diffraction grating that has a periodicity of 270 nm or less and does not diffract the light in the visible region, the structure of the grating being etched either into the bulk of a material or into a material deposited on an organic or mineral substrate of spherical or lamellar form, the interferential screening agent being selected so that the composition has a transmission factor of 80% or more over an interval at least 200 nm wide in the 400-800 nm range.

2. A composition according to claim 1, in which the interferential screening agent is selected so that the composition has a transmission factor of 80% or less for at least one wavelength in the 290-400 nm range.

3. A composition according to claim 1, in which the interferential screening agent is selected so that the composition has a transmission factor of 85% or more, over an interval at least 200 nm wide in the 400-800 nm range; and a transmission factor of 80% or less for at least one wavelength in the 290-400 nm range.

4. A composition according to claim 1, in which the interferential screening agent is selected so that the composition has a transmission factor of 90% or more, over an interval at least 200 nm wide in the 400-800 nm range; and a transmission factor of 80% or less for at least one wavelength in the 290-400 nm range.

5. A composition according to claim 1, in which the transmission factor of the composition is 10% or less, for at least one wavelength in the 290 nm-400 nm range.

6. A composition according to claim 1, in which the transmission factor of the composition is 10% or less, for the whole of the 290 nm-400 nm range.

7. A composition according to claim 1, in which the transmission factor of the composition is 5% or less, for at least one wavelength in the 290 nm-400 nm range.

8. A composition according to claim 1, in which the transmission factor of the composition is 5% or less, for the whole of the 290 nm-400 nm range.

9. A composition according to claim 1, in which the transmission factor of the composition is 1% or less, for at least one wavelength in the 290 nm-400 nm range.

10. A composition according to claim 1, in which the transmission factor of the composition is 1% or less, for the whole of the 290 nm-400 nm range.

11. A composition according to claim 1, in which the transmission factor of the composition is 85% or more, over an interval at least 200 nm wide in the 400 nm-800 nm range.

12. A composition according to claim 1, in which the transmission factor of the composition is 85% or more, over an interval at least 300 nm wide in the 400 nm-800 nm range.

13. A composition according to claim 1, in which the transmission factor of the composition is 85% or more over the whole of the 400 nm-800 nm range.

14. A composition according to claim 1, in which the transmission factor of the composition is 90% or more, over an interval at least 200 nm wide in the 400 nm-800 nm range.

15. A composition according to claim 1, in which the transmission factor of the composition is 90% or more, over an interval at least 300 nm wide in the 400 nm-800 nm range.

16. A composition according to claim 1, in which the transmission factor of the composition is 90% or more over the whole of the 400 nm-800 nm range.

17. A composition according to claim 1, in which the transmission factor of the composition is 95% or more, over an interval at least 200 nm wide in the 400 nm-800 nm range.

18. A composition according to claim 1, in which the transmission factor of the composition is 95% or more, over an interval at least 300 nm wide in the 400 nm-800 nm range.

19. A composition according to claim 1, in which the transmission factor of the composition is 95%, over the whole of the 400 nm-800 nm range.

20. A composition according to claim 1, in which the periodicity of the diffraction grating is 140 nm or less.

21. A composition according to claim 1, in which the diffracting structure comprises at least two diffraction gratings which extend in non-parallel directions.

22. A composition according to claim 1, in which the diffracting structure comprises at least two perpendicular diffraction gratings.

23. A composition according to claim 21, in which the diffraction gratings have different periodicities.

24. A composition according to claim 1, further comprising at least one organic or inorganic complementary sunscreen which is active in the UVA and/or UVB region.

25. A composition according to claim 24, in which the organic screens are selected from anthranilates; cinnamic derivatives; dibenzoylmethane derivatives; salicylic derivatives, camphor derivatives; triazine derivatives; benzophenone derivatives;β, β-diphenylacrylate derivatives; benzotriazole derivatives; benzalmalonate derivatives; benzimidazole derivatives; imidazolines; bis-benzoazolyl derivatives; p-aminobenzoic acid derivatives (PABA); benzoxazole derivatives; methylene bis-(hydroxyphenyl benzotriazole) derivatives; polymeric and silicone screens; dimers derived from α-alkylstyrene; 4,4-diarylbutadienes, and mixtures thereof.

26. A composition according to claim 24, in which the organic screens are selected from:
    ethylhexyl salicylate,
    ethylhexyl methoxycinnamate,
    octocrylene,
    butyl methoxydibenzoylmethane,
    phenylbenzimidazole sulfonic acid,
    benzophenone-3,
    benzophenone-4,
    benzophenone-5,
    n-hexyl 2-(4-diethylamino-2-hydroxybenzoyl)-benzoate,
    4-methylbenzylidene camphor,
    terephthalylidene dicamphor sulfonic acid,
    disodium phenyl dibenzimidazole tetra-sulfonate,
    2,4,6-tris-(diisobutyl 4'-amino benzalmalonate)-s-triazine anisotriazine,
    ethylhexyl triazone,
    diethylhexyl butamido triazone,
    methylene bis-benzotriazolyl tetramethylbutylphenol,
    drometrizole trisiloxane,
    polysilicone-15,
    1,1-dicarboxy-(2',2'-dimethyl-propyl)-4,4-diphenylbutadiene,
    2,4-bis-[5-1-(dimethylpropyl)benzoxazol-2-yl-(4-phenyl)-imino]-6-(2-ethylhexyl)-imino-1,3,5-triazine; and mixtures thereof.

27. A composition according to claim 24, in which the inorganic screens are selected from coated or non-coated pigments or nanopigments of metal oxides.

28. A composition according to claim 24, in which the complementary inorganic screens are nanopigments of amorphous or crystalline titanium oxide in the rutile and/or anatase form, iron oxide, zinc oxide, zirconium oxide, or cerium oxide.

29. A composition according to claim 1, wherein the composition also contains at least one agent for artificially bronzing and/or tanning the skin.

30. A composition according to claim 1, wherein the composition also contains at least one cosmetic adjuvant selected from organic solvents, ionic or non-ionic thickening agents, softeners, moisturizers, opacifying agents, stabilizing agents, emollients, silicones, insect repellents, fragrances, preservatives, surfactants, fillers, pigments, polymers, propellants, alkalinizing or acidifying agents or any other ingredient in normal use in the cosmetic and/or dermatological field.

31. A composition according to claim 1, wherein the composition is in the form of a lotion or serum, aqueous gel, oil-in-water or water-in-oil emulsion, multiple emulsions, microemulsions, ionic and/or non-ionic type vesicular dispersions, or wax/aqueous phase dispersions.

32. A composition according to claim 1, wherein the composition is in the form of an oil-in-water or water-in-oil emulsion comprising at least 1% by weight with respect to the total composition weight of emulsifying surfactant.

33. An interferential screening agent comprising a diffracting interferential structure comprising at least one diffraction grating that does not diffract the light in the visible region, said diffracting interferential structure arranged so that the screening agent has:
   a transmission factor of 80% or less for at least one wavelength in the 290-400 nm range; and
   a transmission factor of 80% or more, over at least one interval of at least 200 nm wide in the 400-800 nm range,
   the interferential structure comprising at least one diffraction grating having a periodicity of 270 nm or less, the structure of the grating being etched either into the bulk of a material or into a material deposited on an organic or mineral substrate of spherical or lamellar form.

34. An agent according to claim 33, in which the periodicity of the diffraction grating is 140 nm or less.

35. An agent according to claim 33, in which the diffracting structure comprises at least two diffraction gratings.

36. An agent according to claim 33, in which the diffracting structure comprises at least two perpendicular diffraction gratings.

37. A method to increase a sun protective factor of a cosmetic or dermatological composition comprising introducing in the composition at least one diffracting interferential screening agent, which screens UVA and/or UVB,
   said screening agent comprising at least one diffraction grating that has a periodicity of 270 nm or less and does not diffract the light in the visible region, the structure of the grating being etched either into the bulk of a material or after depositing a material on an organic or mineral substrate of spherical or lamellar form, the interferential screening agent being selected so that the composition has a transmission factor of 80% or more over an interval at least 200 nm wide in the 400-800 nm range.

* * * * *